(12) United States Patent
Tillotson et al.

(10) Patent No.: US 7,148,059 B1
(45) Date of Patent: Dec. 12, 2006

(54) MYOCYTE CULTURE PACING APPARATUS

(75) Inventors: Douglas L. Tillotson, Milton, MA (US); Richard T. Udale, Roslindale, MA (US); Frederick A. Haer, Quincy, MA (US); Katherine L. Worden, Randolph, MA (US)

(73) Assignee: IonOptix Corporation, Milton, MA (US)

( * ) Notice: Subject to any disclaimer, the term of this patent is extended or adjusted under 35 U.S.C. 154(b) by 537 days.

(21) Appl. No.: 10/371,916

(22) Filed: Feb. 21, 2003

Related U.S. Application Data

(60) Provisional application No. 60/359,072, filed on Feb. 22, 2002.

(51) Int. Cl.
*C12M 1/34* (2006.01)

(52) U.S. Cl. .............................. 435/288.3; 435/288.4; 204/403.01; 204/412

(58) Field of Classification Search .................... None
See application file for complete search history.

(56) References Cited

U.S. PATENT DOCUMENTS 4,335,206 A * 6/1982 Wilkins et al. ............... 435/34
5,304,486 A * 4/1994 Chang ...................... 435/285.2
5,432,086 A * 7/1995 Franzl et al. ............. 435/286.2
6,686,193 B1 * 2/2004 Maher et al. ............. 435/285.2

FOREIGN PATENT DOCUMENTS

JP          02-084168       *  3/1990

* cited by examiner

*Primary Examiner*—David Redding
(74) *Attorney, Agent, or Firm*—Michael W. Ferrell

(57) ABSTRACT

A myocyte culture pacing apparatus operating in conjunction with a standard culture dish that permits long term maintenance of cultured myocyte cells over a period of several weeks The device includes a base unit for receiving the culture dish, and an electrode unit for placement atop the culture dish which can receive the cover of the culture dish. The electrode unit has a first and a second planar conductive electrodes extending into each well of the culture dish. The electrodes are planar and extend across the width of the well and are connected to electrical connector for connection to an external electronic unit, which supplies the a variety of electrical pulse regimes to pace the myocyte cultures. The electronic unit permits the type, frequency, duration, voltage and the current of the pulses to be varied in accordance with the desired pacing regime.

18 Claims, 7 Drawing Sheets

MYOCYTE CULTURE PACING APPARATUS

REFERENCE TO RELATED APPLICATIONS

This application claims priority of U.S. Provisional application No. 60/359,072 filed Feb. 22, 2002.

BACKGROUND AND SUMMARY OF THE INVENTION

The present invention is directed to apparatus for providing electrical stimulation to cultures of myocytes, which are contractile biological cells, such as muscle and heart cells.

Much of basic cardiac research is being done at the cellular level with many researchers using isolated cardiac myocytes in culture as their experimental material. Whereas non-beating myocytes in culture de-differentiate and atrophy over time, it has been shown that electrically stimulated, continuously beating myocytes maintain their morphology and contractility and retain their normal protein synthesis levels. The useful life span of the myocytes in culture is thus increased by many days. By proposing the design of a device for providing electrical stimulation "pacing" to myocyte cultures, this apparatus provides a unique but basic tool that will make chronic pacing of cultured myocytes an affordable and convenient technique to the cardiac research community.

The intense interest in understanding the physiology and patho-physiology of the heart has led to a substantial increase in the number of laboratories that study the myocardium at the cellular level using isolated cardiac myocytes. Culturing cardiac myocytes in serum-free, well-defined media is the method of choice for studying cell physiology and metabolism under tightly controlled experimental conditions. Developed in the seventies and eighties, the applications for myocyte culture have grown explosively and Myocyte culture is now a mainstream technique.

There exist two primary needs for a Myocyte culture pacing apparatus of the type described herein. The first is the ability for long term maintenance of cultured cells over a period of several weeks. Second, a Myocyte culture pacing apparatus is needed to allow laboratories to scale up the quantity of myocytes cultured. Many experiments require a long-term, stable, preparation of myocytes. These include myofilament gene transfer with the use of adeno-viruses, studies on the regulation of protein turnover, protein incorporation, or the hypertrophic effect of a specific drug or treatment, It has long been known that adult cardiac myocytes can be cultured for more than a month in the presence of serum. Unfortunately, serum is not a very well defined medium. Serum also contains many trophic factors, which is undesirable when studying processes related to growth. This has led most laboratories to perform their long-term studies with embryonic or neonatal cells, which can be cultured in serum-free media. However, extrapolation from embryonic or neonatal myocytes to the fully differentiated myocardium is problematic. Embryonic or neonatal cells so strongly differ in morphology from fully differentiated cells that it is not possible to measure important functional parameters such as contractility. Also, the expression of ion channels and contractile protein isoforms changes during cell development.

The alternative is the culture of adult myocytes in serum free media. Much progress has been made over the past years and myocytes can be kept viable now for several weeks. Problems that remain are low survival rates and atrophy. Atrophy results in a loss of regular myofibrilar structure which manifests itself as a disappearance of the striation pattern. Therefore a substantial need exists for alternative methods of long-term culture that do retain the typical characteristics of adult cardiac myocytes. Chronic pacing has emerged as a possible solution for the above problems.

Adult cardiac myocytes that are cultured without the presence of growth factors require mechanical stimuli to prevent atrophy. Pacing the cell with electrical pulses provides such a stimulus. Long term electrical stimulation of myocytes plated in serum-free media has been shown to prolong the viability of the cells, retain cell phenotype, and keep levels of protein synthesis comparable to that of the intact heart. Contractility is preserved and important functional parameters such as amplitude of contraction and peak calcium current are increased compared to non-paced cells in culture. Photomicrographs were made of a cell that was beating at 1 Hz and a non-paced quiescent myocyte, from the same animal, after a week of culture. The paced myocyte retained its size and still had a clearly striated myofibrilar content, where the quiescent cell had a rounded appearance and was seen to be losing its striation pattern. The underlying process was found to be that in the quiescent cell the rate of protein synthesis was reduced, leading to a loss in total protein, whereas chronic pacing lead to a recovery and subsequent steady state level of protein synthesis.

The ideal stimulator for long term pacing has several qualities. One of the key issues is that cell culture takes place in a closed system. Byproducts of the electrical field such as the generation of protons or oxygen radicals, and heat production have to be minimized. Several strategies will be applied in the Myocyte culture pacing apparatus.

Heat production and oxidation products are largely a function of the properties of the electrode which have been redesigned in the present invention. Proton accumulation due to electrolysis is avoided by reversing the polarity between pulses, a solution that is not available on any commercial stimulators. Another potential problem is current leakage between pulses, while this is not an issue with continuous perfusion, it is unacceptable in a closed system because it will heat up the preparation. These problems are addressed in the present design.

Experiments using electrical stimulation are normally done using continuous superfusion that serves among other things to remove the oxidative products generated during (and between) pacing stimuli. Continuous superfusion can not be done conveniently in the cell culture incubator. Consequently, special care must be taken to avoid the generation of oxidative products (principally protons and oxygen radicals) in the culture-pacer design. Small Platinum electrodes are typically used for field stimulation during cellular experimentation. However, at the high voltages used in the present Myocyte culture pacing apparatus small sized platinum electrodes will generate too many oxidation products toxic to the cells. The present electrode unit preferably uses large size chemically and biologically inert carbon electrodes which do not generate deleterious oxidation products. The electrodes can also be cleaned and autoclaved for repeated use.

Cultured myocytes can be used for protein assays or for quantitative analysis of other cellular products (e.g. mRNA). Such experiments require a large number of cells due to the typically minute amount of material present in a single cell. These quantities are then multiplied by the number of treatments or time-points the researcher decides to compare.

From an economical and statistical point of view, it is desirable to make as many valid measurements as possible from one single animal or at least within one experiment. One great difficulty the researcher is presented with is the large power required from the stimulator to scale up the quantity of paced cells. This points to the need for a pacing instrument that can provide many high voltages output channels and the means to distribute them to myocytes in culture dishes.

No electronic stimulator that is currently available is suitable for pacing large quantities of cells, or cells in long-term culture. The function of a standard cell stimulator is to provide electrical stimuli to a wide range of physiological applications, from muscle fibers to neurons. To cater to such a variety of applications, standard stimulators usually support the generation of quite sophisticated voltage waveforms. The result of this admirable flexibility is a user interface which tends to be more complex than necessary for the simple waveforms required from the present myocyte culture pacing apparatus. A second common assumption in the design of standard stimulators is that they will be used on small preparations. The maximum voltage and current throughput available from these devices simply is not sufficient for field stimulation of whole culture flasks.

The present myocyte culture pacing apparatus satisfies the following specific aims:

1. Provide adjustable output voltage and current in order to work with standard culture dishes or flasks, and different preparations.

2. Provide high voltage, high current throughput to allow multiple preparations or large volumes to be paced 3. Minimize the oxidative products that naturally accumulate during prolonged stimulation in a "closed system". This is achieved by the use of appropriate electrode material, alternating pulse polarity and employing circuitry that guarantees no current leakage between pulses.

4. The present myocyte culture pacing apparatus can serve as a stand-alone, programmable instrument that, once programmed, requires no monitoring.

5. the present apparatus has simple and straightforward user controls to minimize training time and protocol input errors.

Currently no commercial device is available for chronic pacing of cardiac myocytes that meets these aims. The present device will therefore be an enhancement for laboratories worldwide. The present device enables greater flexibility and economy in the use of cultured cardiac myocytes for heart studies.

The present invention is directed to myocyte culture pacing apparatus operating in conjunction with a standard culture dish that permits long term maintenance of cultured cells over a period of several weeks The device includes a base unit for receiving the culture dish, and an electrode unit for placement atop the culture dish which can receive the cover of the culture dish. The electrode unit has a first and a second planar conductive electrodes extending into each well of the culture dish. The electrodes are planar and extend across the width of the well and are connected to electrical connector for connection to an external electronic unit, which supplies the a variety of electrical pulse regimes to pace the myocyte cultures. The electronic unit permits the type, frequency, duration, voltage and the current of the pulses to be varied in accordance with the desired pacing regime.

BRIEF DESCRIPTION OF THE DRAWINGS

For a better understanding of the invention reference is made to the following drawings which are to be taken in conjunction with the detailed description to follow.

DESCRIPTION OF THE PREFERRED EMBODIMENTS

The present myocyte culture pacing apparatus comprises an electronic unit, which supplies the electrical pulses used to pace the myocyte cultures, and an electrode unit which mates with standard culture dishes to contact the cell cultures.

Electronics

Figure 1A:
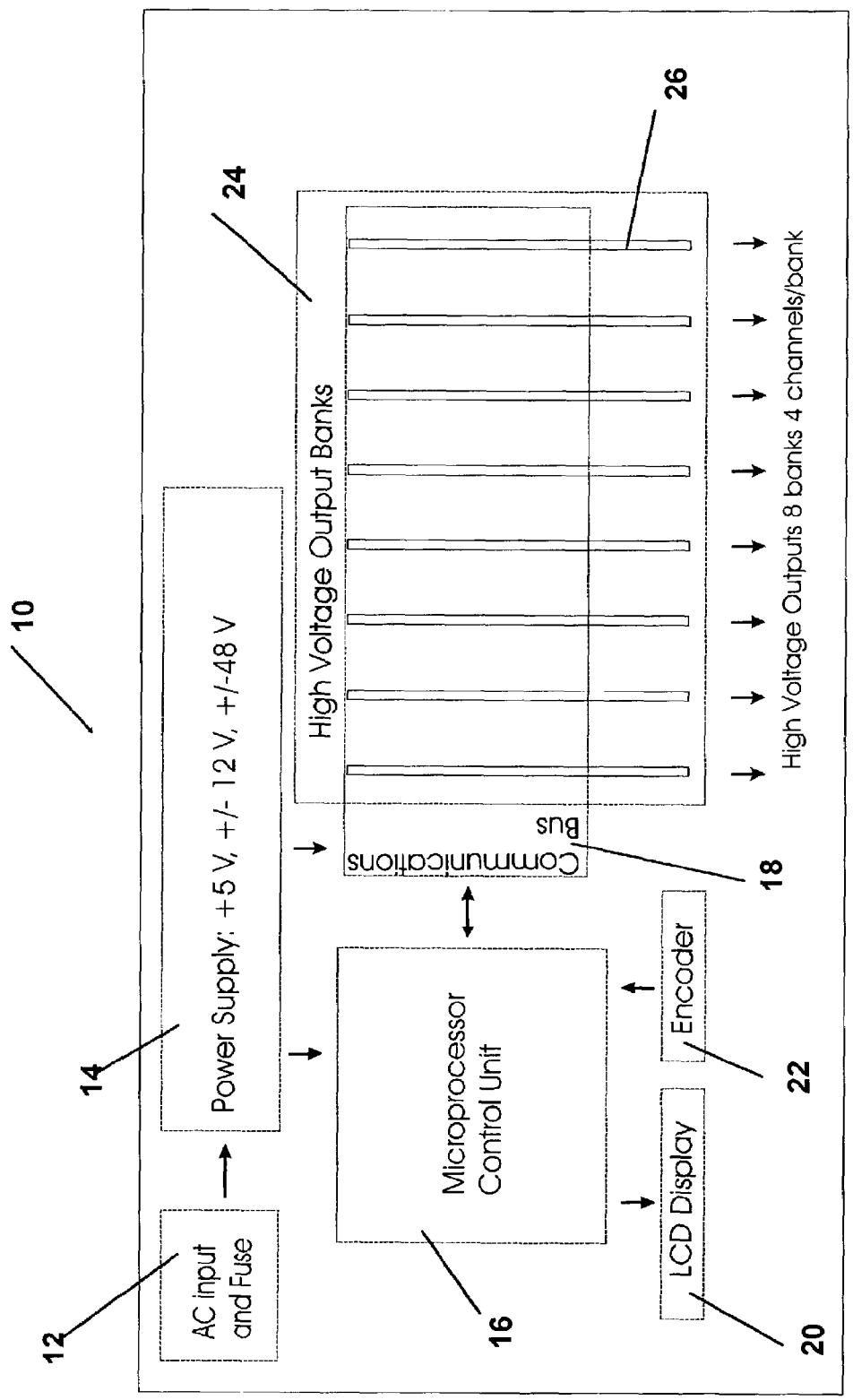
FIG. 1a of the drawings is a block diagram of the electronics of the myocyte culture pacing apparatus of the present invention.

FIG. 1a of the drawings shows a block diagram of the electronics 10 of the myocyte culture pacing apparatus of the present invention. Normal AC power is input at block 12, which in turn drives a power supply unit 14 which provides the appropriate DC voltages to a microprocessor control unit 16 and through a communications bus 18 to a high voltage output bank 24, to which to high voltage boards 26 are connected. An encoder 22 is operated by the user to input the desired pacing parameters, which are displayed on an LCD display 20. The LCD display 20 displays the current frequency, voltage, polarity, pulse duration and enable status of one or more independent pulse trains. Encoder 22 is a button that turns and clicks to scroll through the display and edit properties. Microprocessor control unit 16 monitors and interprets encoder use and appropriately updates display 20 and sends the property changes to the high voltage boards 26.

Communications bus 18 provides a pathway from control unit 16 to high voltage boards 26 for power and communication through a RS-485 protocol. Each board 26 of high voltage output banks 24 contains a microprocessor unit to interpret commands from microprocessor control unit 16 and to use internal timing to control the output pulse train. Each board 26 also contains a high voltage output unit consisting of a Digital to Analog converter, a high voltage supply, reed relays to provide complete zero voltage isolation and a standard connector to connect to up to four electrode units described below. High-voltage output banks 24 generate voltage pulses between 40 and 50 volts. The current of output pulses are limited to 100 milliamps. As high voltage boards 26 are separate, communication bus 18 can deliver independent pacing regimens (pulse trains) to differing high voltage boards 26.

Figure 1B:
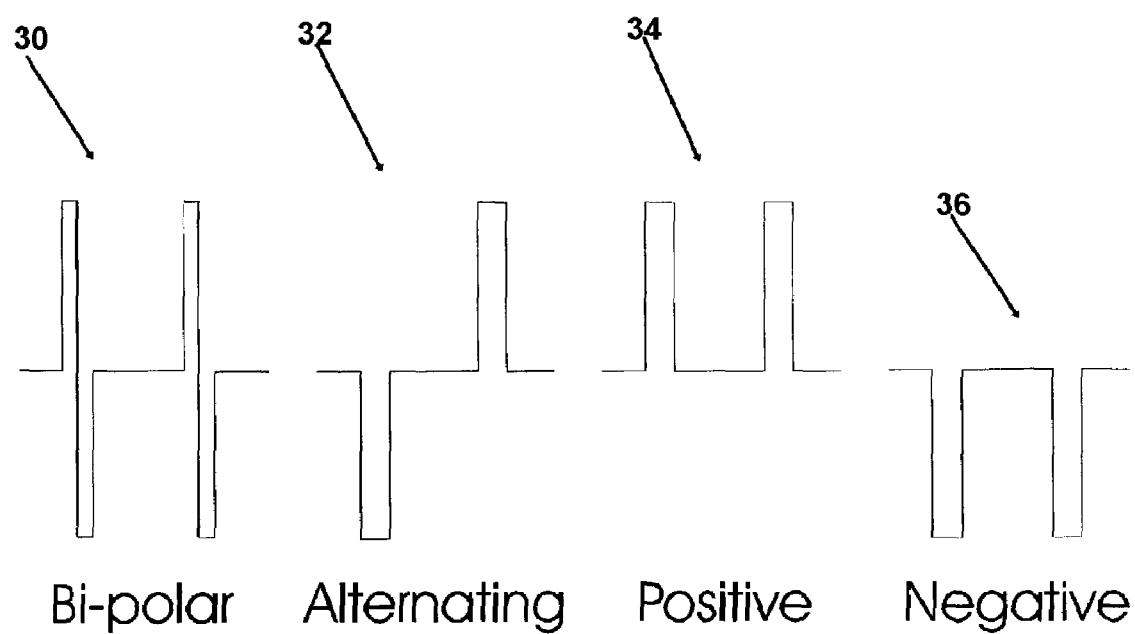
FIG. 1b illustrates samples of the output waveforms which may be applied to the electrode units of the myocyte culture pacing apparatus of the present invention and thus to the myocyte cultures to pace same.

FIG. 1b illustrates samples of the output waveforms which may be applied to the electrode units and thus to the myocyte cultures to pace same. Waveform 30 is a series of bipolar pulses in which a first positive going pulse is immediately reversed into a negative going pulse. Waveform 32 is a series of alternating positive and negative pulses. Waveform 34 is a series of all positive pulses and waveform 36 is a series of all negative pulses. Microprocessor control unit 16 permits control of the frequency, voltage, polarity and duration of the selected waveform.

In the Myocyte culture pacing apparatus of the present invention, the digital control logic provides the following functions:

1. Manage user control and display of pacing parameters;
2. Allow the programming and storage of several pacing protocols
3. Control digital-to-analog converter to set output voltage for the amplifier;
4. Provide timed control signals to enable each output amplifier;
5. Monitor and display current output for all enabled amplifiers;
6. Monitor for error conditions such as open circuit and excessive output current.

The digital control unit 16 can be implemented using one or more high-performance microcontrollers. Microcontrollers provide all the circuitry required to implement a complete programmable control system on a single chip. These chips include modern development tools that allow the device to be programmed and debugged in high-level languages such as C. The advantage of this type of control is flexibility. It will allow users to use a simple front panel interface to create multiple pacing protocols, define alarm conditions that specify acceptable ranges of output current for their particular situation, and program timers to initiate and end protocols. The microcontroller's ability to communicate through a standard RS-232 communications port means that, in addition to front panel control and display, the parameters can be loaded from, or saved to, an external computer. Microcontrollers also offer flexibility in terms of future upgrading. In many cases, options and available parameters can be added or altered by software updates without any change in hardware. The addition of extra output channels is also possible with little additional hardware complexity.

Electrodes

Figure 2:
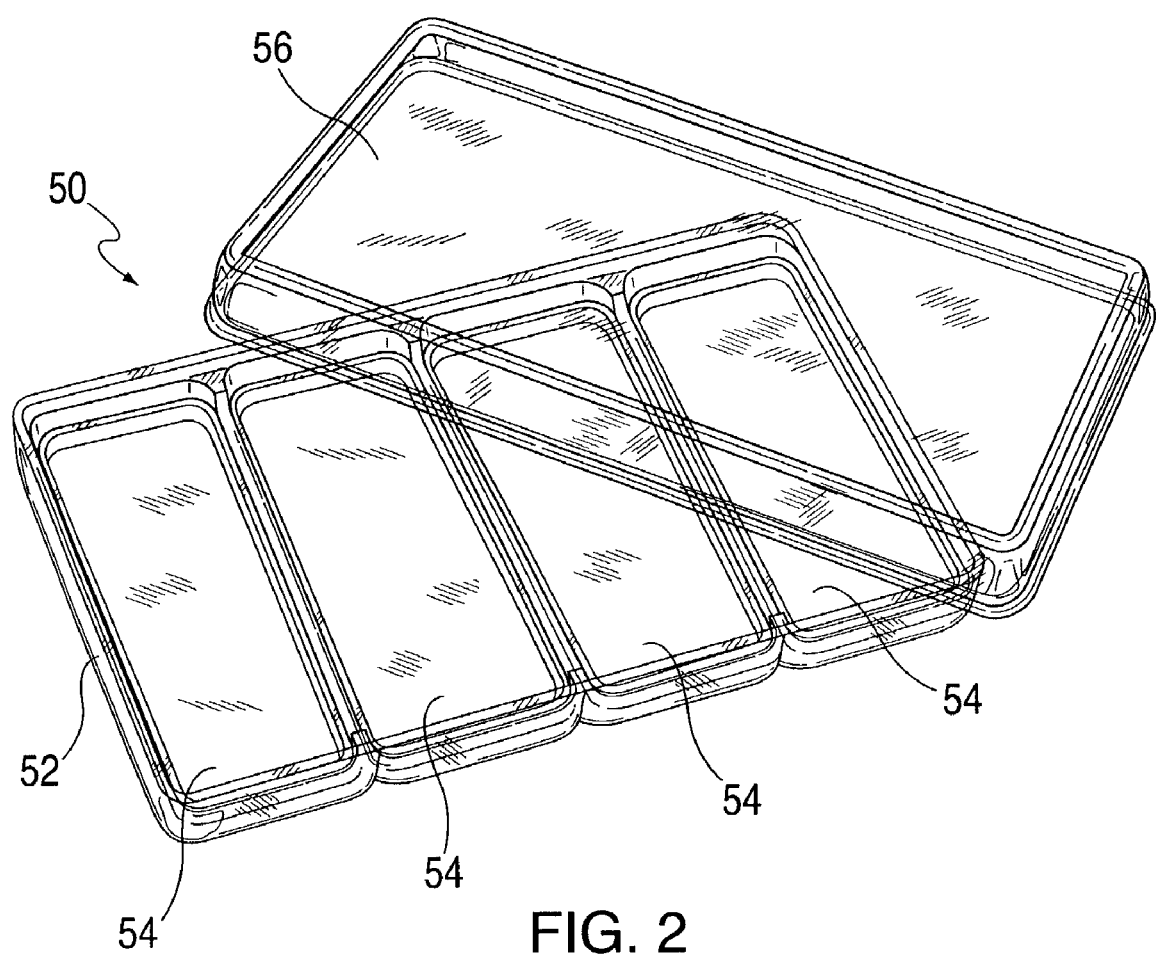
FIG. 2 illustrates a standard four well culture having multiple wells for holding the myocytes and their solution, each well being physically isolated from the others.
Figure 3:
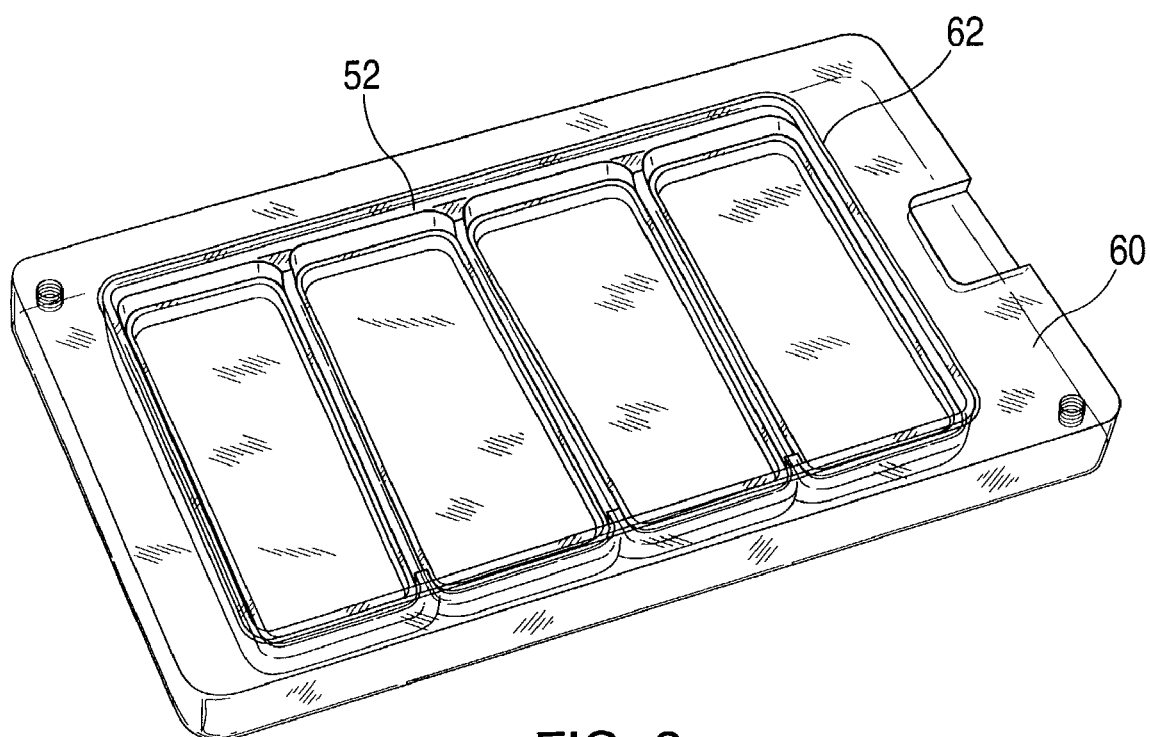
FIG. 3 illustrates the base of a culture dish fitted within a base of the present invention.

FIG. 2 illustrates a standard four well culture dish 50 which includes a lower portion 52 having multiple wells 54 for holding the myocytes and their solution, each well 54 being physically isolated from the others. Culture dish 50 also includes a cover 56 which fits atop base 52 and serves to close off wells 54. FIG. 3 illustrates base 52 of culture dish fitted within a base 60 of the present invention. Base 60 of the present invention includes an opening 62 into which base 54 of culture dish 50 fits and which permits the removal and replacement of culture dishes 50.

Figure 4:
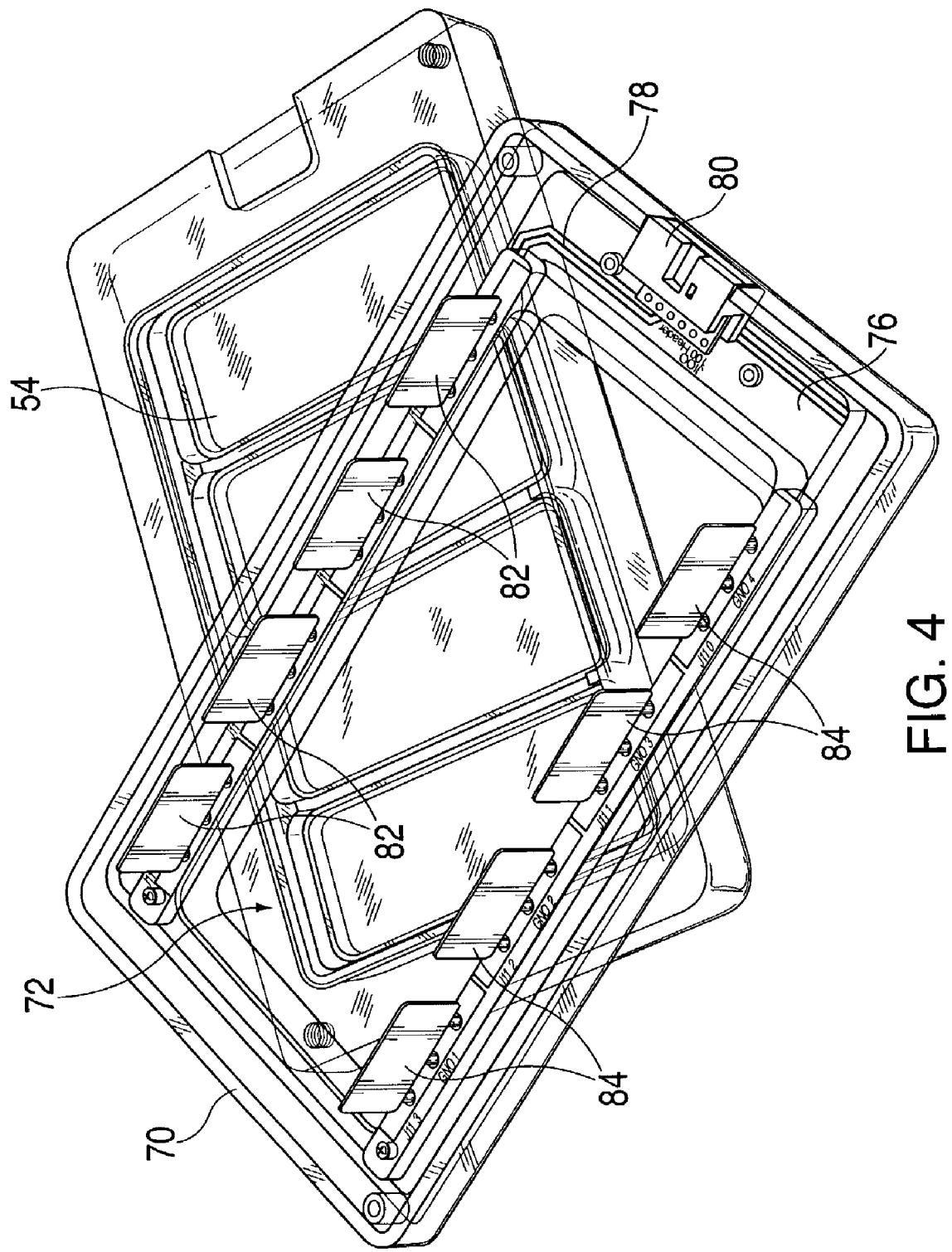
FIG. 4 illustrates the cover unit of the present apparatus inverted to show the electrodes and sitting atop the units illustrated in FIG. 3.
Figure 5:
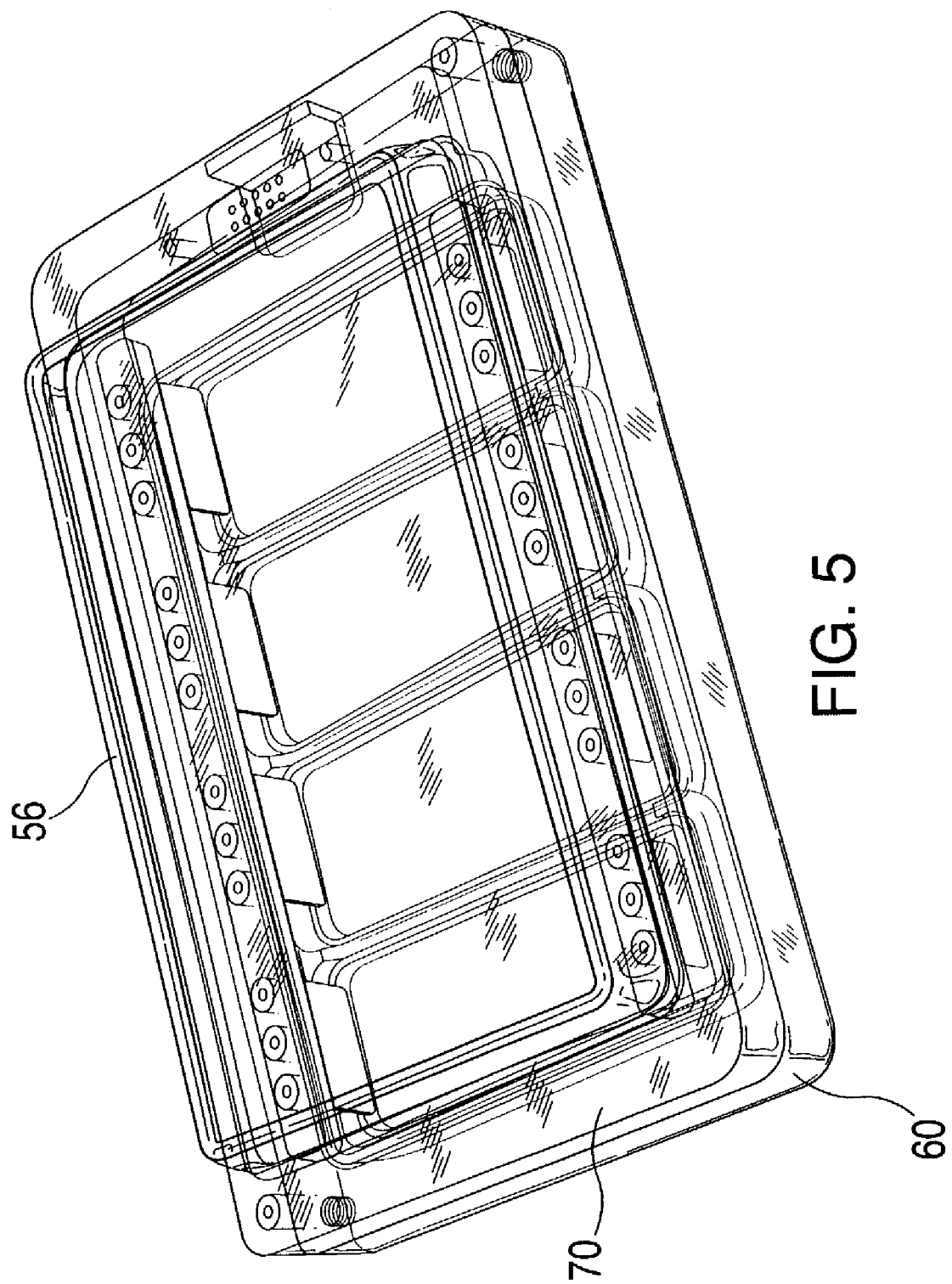
FIG. 5 illustrates the assembled myocyte culture pacing apparatus of the present invention.
Figure 6:
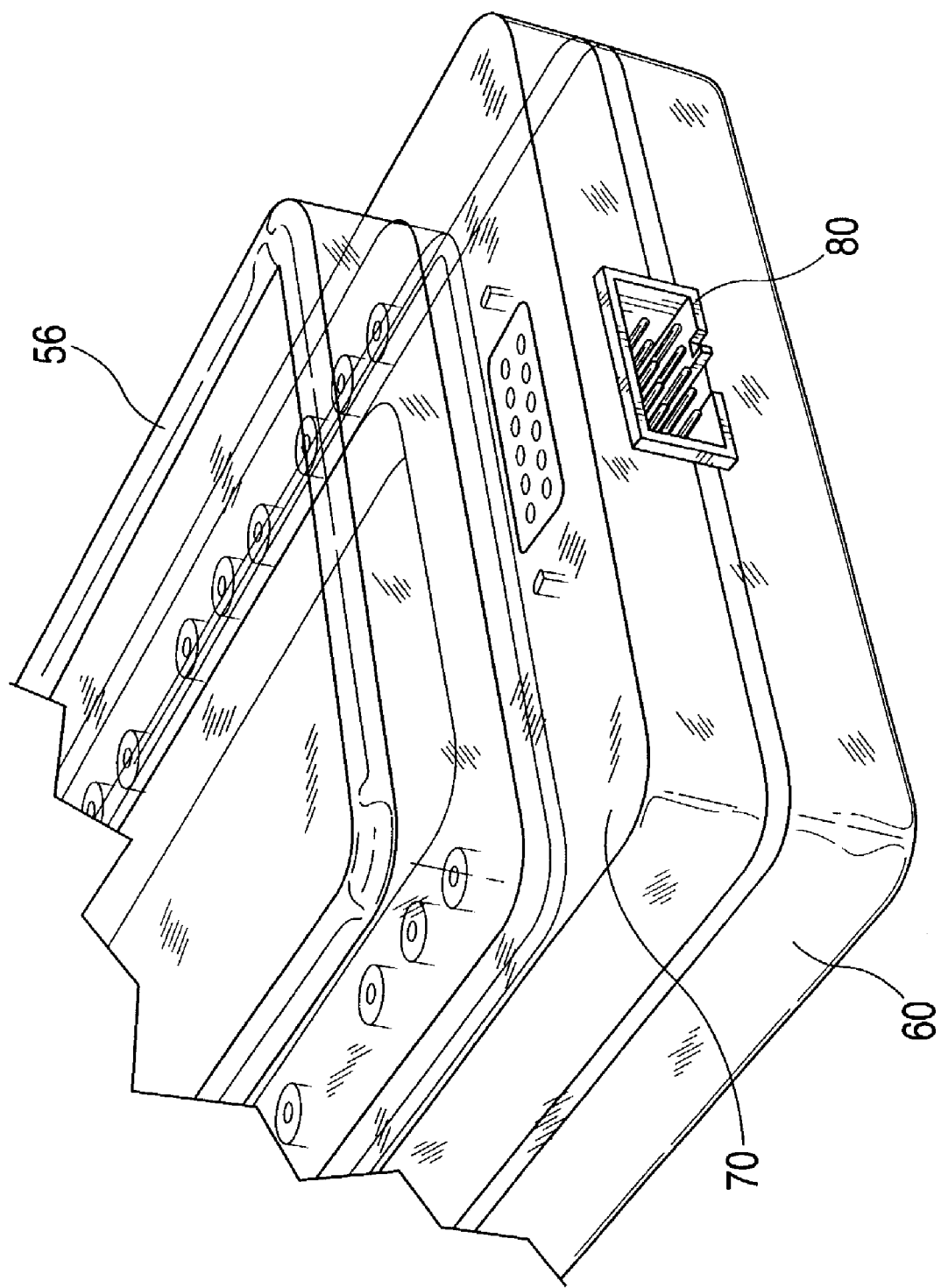
FIG. 6 illustrates the end showing the electrical connector of the apparatus of the present invention.

FIG. 4 illustrates the cover unit 70 of the present apparatus which has been inverted and is sitting atop the units illustrated in FIG. 3. Cover unit 70 is designed to mate with base unit 60 so that lower portion 54 of culture dish 50 is positioned between cover unit 70 and base unit 60 of the present apparatus. Cover unit 70 includes a central opening 72 which permits access to wells 54 of culture dish 50. As is best seen in FIGS. 5 and 6 the upper surface of cover unit 70 includes a lip for engagement with cover 56 of culture dish 50 so that it again functions to cover wells 54. As such, the assembly consists of base unit 60 of electrode assembly 50, lower portion 52 of culture dish 50, cover unit 70 of electrode assembly 50 and cover 56 of culture dish 50. As each of the units of myocyte culture pacing apparatus of the present invention is preferably molded from transparent material such as glass or Lucite, this arrangement enables the entire electrode assembly and culture dish to be placed on a microscope stage for observation, with cover 56 removed, without interruption of pacing.

As shown in FIG. 4 cover 70 of electrode assembly 60 is inverted to show the electronics contained therein. Disposed on the underside of cover 70 is a U-shaped printed circuit board 76 which carries conductive traces 78 which lead from a standard electrical connector 80 (used to connect to the drive electronics) to a series of four positive electrodes 82 and four negative electrodes 84 which are upstanding from circuit board 76. Thus, one positive electrode 82 and one negative electrode 84 will extend downwardly into opposed ends of each well 54 of culture dish 50 in use. Electrodes 82, 84 are preferably wide so as to have a large surface area and extend across the width of each well 54 and are formed from durable conductive material such as chemically and biologically inert solid carbon which will minimize possible contamination of the cell cultures by the electrodes. In another embodiment, the electrodes can comprise solid platinum wires wrapped about a chemically and biologically inert material such as certain plastics. In certain applications the electrodes can be stainless steel plated with an inert conductive material such as gold or platinum or carbon. After assembly, printed circuit board 76 may be "potted" (sealed under a layer of material) with a suitable inert material, such as silicone, to prevent contamination of the cultures and to enable electrode assembly 60 to tolerate sterilizing in an autoclave.

The invention herein has been illustrated with respect to a standard four well rectangular culture dish, it is to be understood that by suitable modification of the dimensions of the present invention the invention can be utilized with other culture dishes of differing configurations. A single voltage amplifier can drive multiple electrode assemblies and a single control circuit can control multiple voltage amplifiers so that the controlled pacing of a large number of myocytes is readily accomplished The invention has been described with respect to preferred embodiments. However, as those skilled in the art will recognize, modifications and variations in the specific details which have been described and illustrated may be resorted to without departing from the spirit and scope of the invention as described herein.

What is claimed is:

1. Apparatus for pacing a myocyte culture contained in a plurality of wells of a multi-well culture dish comprising:
   a) a base unit for receiving the culture dish;
   b) an electrode unit for placement atop the culture dish and having a central opening, said electrode unit having a plurality of first conductive electrodes made from a chemically and biologically inert material disposed on a first edge of the opening and a plurality of second conductive electrodes made from a chemically and biologically inert material disposed on a second edge of the opening opposite the plurality of first electrodes, the electrodes being adapted for extending into each well of the culture dish, one of the plurality of first electrodes being disposed at one end of each well with one of the plurality of second electrodes being disposed at the opposite end of each well, each of said electrodes being substantially planar and extending across the width of the well;

c) an electrical connector for connection to external apparatus for providing a stream of electrical pulses to provide pacing to the myocyte culture; and d) means for electrically connecting each of the first and second electrodes to the electrical connector;

wherein the means for electrically connecting each of the plurality of first conductive electrodes and the plurality of second conductive electrodes to the electrical connector comprise a printed circuit board disposed in the electrode unit upon which the first and second plurality of electrodes are mounted;

and further wherein the printed circuit board disposed in the electrode unit is sealed there within by means of a biologically inert compound.

2. The pacing apparatus as claimed in claim 1 wherein the central opening permits access to the wells of the culture dish.

3. The pacing apparatus as claimed in claim 2 wherein the electrode unit has means for receiving the cover of the culture dish so as to cover the central opening of the electrode unit.

4. The pacing apparatus as claimed in claim 1 wherein the plurality of first conductive electrodes and the plurality of second conductive electrodes comprise chemically and biologically inert carbon material.

5. The pacing apparatus as claimed in claim 1 wherein the plurality of first conductive electrodes and the plurality of second conductive electrodes comprise platinum wire wrapped about a wafer of biologically inert material.

6. The pacing apparatus as claimed in claim 1 wherein the plurality of first conductive electrodes and the plurality of second conductive electrodes are rectangular in plan view.

7. The pacing apparatus as claimed in claim 1 wherein the external apparatus for providing a stream of electrical pulses to provide pacing to the myocyte culture comprises means to permit at least one of: the frequency, the duration, the voltage and the current of the pulses to be varied.

8. The pacing apparatus as claimed in claim 1 wherein the external apparatus for providing a stream of electrical pulses provides at least one of the following pulse types: bipolar, alternating between positive and negative, all positive, and all negative.

9. The pacing apparatus as claimed in claim 1 wherein the base unit and the electrode unit are transparent.

10. Apparatus for pacing a myocyte culture contained in a plurality of wells of a multi-well culture dish comprising:

a) an electrode unit for placement atop the culture dish and having a central opening, said electrode unit having a plurality of first conductive electrodes made from a chemically and biologically inert material disposed on a first edge of the opening and a plurality of second conductive electrodes made from a chemically and biologically inert material disposed on a second edge of the opening opposite the plurality of first electrodes, the electrodes being adapted for extending into each well of the culture dish, one of the plurality of first electrodes being disposed at one end of each well with one of the plurality of second electrodes being disposed at the opposite end of each well, each of said electrodes being substantially planar and extending across the width of the well; and b) means for providing a stream of electrical pulses to the first and second electrodes to provide pacing to the myocyte culture;

wherein the means for providing a stream of electrical pulses to the first and second electrodes comprise a printed circuit board disposed in the electrode unit upon which the first and second plurality of electrodes are mounted;

and further wherein the printed circuit board disposed in the electrode unit is sealed there within by means of a biologically inert compound.

11. The pacing apparatus as claimed in claim 10 wherein the means for providing a stream of electrical pulses to provide pacing to the myocyte culture comprises means to permit at least one of: the frequency, the duration, the voltage and the current of the pulses to be varied.

12. The pacing apparatus as claimed in claim 10 wherein the means for providing a stream of electrical pulses to provide pacing to the myocyte culture provides at least one of the following pulse types: bipolar, alternating between positive and negative, all positive, and all negative.

13. The pacing apparatus as claimed in claim 10 further including an electrical connector disposed on said electrode unit for releasable connection to the means for providing a stream of electrical pulses.

14. The pacing apparatus as claimed in claim 10 wherein the plurality of first conductive electrodes and the plurality of second conductive electrodes comprise chemically and biologically inert carbon material.

15. The pacing apparatus as claimed in claim 10 wherein the plurality of first conductive electrodes and the plurality of second conductive electrodes comprise platinum wire wrapped about a wafer of biologically inert material.

16. The pacing apparatus as claimed in claim 10 wherein the plurality of first conductive electrodes and the plurality of second conductive electrodes are rectangular in plan view.

17. The pacing apparatus as claimed in claim 10 wherein the means for providing a stream of electrical pulses include a high voltage bank, a plurality of output cards releasably mounted to the a high voltage bank, each output card being connected to one or more electrode units.

18. The pacing apparatus as claimed in claim 17 wherein the means for providing a stream of electrical pulses include a microprocessor control unit for controlling the output of the output cards.

* * * * *